(12) United States Patent
Huffstetler et al.

(10) Patent No.: US 11,672,860 B2
(45) Date of Patent: Jun. 13, 2023

(54) DRUG ELUTING MATRIX ON ANALYTE INDICATOR

(71) Applicant: Senseonics, Incorporated, Germantown, MD (US)

(72) Inventors: Philip Huffstetler, Germantown, MD (US); Sanat Mohanty, Germantown, MD (US); Robert Attwood, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 612 days.

(21) Appl. No.: 16/671,279

(22) Filed: Nov. 1, 2019

(65) Prior Publication Data

US 2020/0138948 A1 May 7, 2020

Related U.S. Application Data

(60) Provisional application No. 62/754,788, filed on Nov. 2, 2018.

(51) Int. Cl.
*A61K 41/00* (2020.01)
*A61B 5/145* (2006.01)
(Continued)

(52) U.S. Cl.
CPC .......... *A61K 41/0042* (2013.01); *A61B 5/002* (2013.01); *A61B 5/1451* (2013.01);
(Continued)

(58) Field of Classification Search
None
See application file for complete search history.

(56) References Cited

U.S. PATENT DOCUMENTS 5,512,246 A   4/1996  Russell et al.
5,517,313 A   5/1996  Colvin, Jr.
(Continued)

FOREIGN PATENT DOCUMENTS

EP   1637164 A2   3/2006
EP   2303227 A2   4/2011
(Continued)

OTHER PUBLICATIONS

Suzana G. Vallejo-Heligon, Bruce Klitzman, William M. Reichert. "Characterization of porous, dexamethasone-releasing polyurethane coatings for glucose sensors." Acta Biomaterialia, vol. 10, 2014, pp. 4629-4638. (Year: 2014).*

*Primary Examiner* — Isaac Shomer
(74) *Attorney, Agent, or Firm* — Rothwell, Figg, Ernst & Manbeck, P.C.

(57) ABSTRACT

A sensor that may be implanted within a living animal (e.g., a human) and may be used to measure an analyte (e.g., glucose or oxygen) in a medium (e.g., interstitial fluid, blood, or intraperitoneal fluid) within the animal. The sensor may include a sensor housing and an analyte indicator covering at least a portion of the sensor housing. The sensor may include a drug-eluting matrix that covers at least a portion of the analyte indicator. The drug-eluting matrix may include one or more openings configured to allow the medium to pass through the drug-eluting matrix and come into contact with the analyte indicator. The sensor may include one or more therapeutic agents. The one or more therapeutic agents may reduce deterioration of the analyte indicator. The one or more therapeutic agents may be incorporated within the drug-eluting matrix.

20 Claims, 8 Drawing Sheets

(51) Int. Cl.
  *A61B 5/00* (2006.01)
  *A61B 5/1459* (2006.01)
  *A61K 31/573* (2006.01)
  *A61N 5/06* (2006.01)
  *A61K 31/616* (2006.01)
  *A61K 31/192* (2006.01)

(52) U.S. Cl.
  CPC ........ *A61B 5/1459* (2013.01); *A61B 5/14532* (2013.01); *A61K 31/192* (2013.01); *A61K 31/573* (2013.01); *A61K 31/616* (2013.01); *A61N 5/062* (2013.01)

(56) References Cited

U.S. PATENT DOCUMENTS

| | | |
|---|---|---|
| 9,414,775 B2 | 8/2016 | Colvin, Jr. et al. |
| 9,693,714 B2 | 7/2017 | DeHennis et al. |
| 9,931,068 B2* | 4/2018 | Huffstetler ........... A61B 5/1459 |
| 10,842,850 B2* | 11/2020 | Green .................. A61K 31/573 |
| 11,109,779 B2* | 9/2021 | Emken ................. A61B 5/1459 |
| 2008/0228051 A1* | 9/2008 | Shults ..................... A61L 31/16 600/316 |
| 2010/0256779 A1* | 10/2010 | Brauker ................ A61L 31/146 623/23.76 |
| 2013/0241745 A1 | 9/2013 | Colvin, Jr. et al. |
| 2015/0057509 A1* | 2/2015 | Huffstetler ......... A61B 5/14503 600/309 |
| 2017/0173216 A1 | 6/2017 | Ju et al. |
| 2018/0137070 A1 | 5/2018 | DeHennis et al. |
| 2018/0220940 A1 | 8/2018 | Huffstetler et al. |

FOREIGN PATENT DOCUMENTS

| | | |
|---|---|---|
| EP | 1477187 B1 | 7/2011 |
| EP | 2416783 A1 | 2/2012 |
| WO | 2009/139924 A2 | 11/2009 |
| WO | 2010/115615 A1 | 10/2010 |
| WO | 2015/027018 A1 | 2/2015 |
| WO | 2015/156966 A1 | 10/2015 |

* cited by examiner

DRUG ELUTING MATRIX ON ANALYTE INDICATOR

CROSS-REFERENCE TO RELATED APPLICATION

The present application claims the benefit of priority to U.S. Provisional Application Ser. No. 62/754,788, filed on Nov. 2, 2018, which is incorporated herein by reference in its entirety.

BACKGROUND

Field of Invention

The present invention relates generally to measuring an analyte in a medium of a living animal using a system including a sensor implanted or inserted into the living animal. Specifically, the present invention relates to a sensor that utilizes one or more therapeutic agents, which may be incorporated within a drug-eluting matrix applied onto at least a portion of an analyte indicator.

Discussion of the Background

A sensor may be implanted within a living animal (e.g., a human) and used to measure an analyte (e.g., glucose, oxygen, cardiac markers, low-density lipoprotein (LDL), high-density lipoprotein (HDL), or triglycerides) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entirety.

A sensor may include an analyte indicator, which may be in the form of indicator molecules embedded in an analyte indicator (e.g., a graft, layer, or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the animal's immune system may begin to attack the sensor. For instance, if a sensor is implanted in a human, white blood cells may attack the sensor as a foreign body, and, in the initial immune system onslaught, neutrophils may be the primary white blood cells attacking the sensor. The defense mechanism of neutrophils includes the release of highly caustic substances known as reactive oxygen species. The reactive oxygen species include, for example, hydrogen peroxide.

Hydrogen peroxide and other reactive oxygen species may degrade the indicator molecules of an analyte indicator. For instance, in indicator molecules having a boronate group, hydrogen peroxide may degrade the indicator molecules by oxidizing the boronate group, thus disabling the ability of the indicator molecule to bind glucose. Boronic acid degradation may limit the in vivo functionality of the analyte indicator and causation for premature removal and replacement.

Glucocorticoids are used with cardiac pace makers and eye surgery to reduce inflammation. For instance, the following European patent application publications describe pace-maker leads and controlled release of steroids: EP2416783 A1 ("Improved glucocorticoid therapy"), EP1477187 B1 ("Formulation for controlled release of drugs by combining hydrophilic and hydrophobic agents"), EP1637164 A2 ("Improved formulation for controlled release of drugs by combining hydrophilic and hydrophobic agents"), and EP2303227 A2 ("Controlled release corticosteroid compositions and methods for the treatment of optic disorders"). However, these devices do not have analyte indicators, and the glucocorticoid is not used to reduce degradation of an analyte indicator. Instead, the glucocorticoid is used to stop scar tissue from building up.

There is presently a need in the art for improvements in reducing analyte indicator degradation.

SUMMARY

The present invention overcomes the disadvantages of prior systems by providing, among other advantages, reduced analyte indicator degradation. In some embodiments, the advantages may be achieved by applying a drug-eluting matrix directly over the analyte sensing component of an analyte sensor. In some embodiments, the drug-eluting matrix may be configured such that sensor accuracy is maintained and sensor longevity is extended due to mitigation of the localized in vivo immune response of the drug.

One aspect of the present invention may provide a sensor for measurement of an analyte in a medium within a living animal. The sensor may include a sensor housing, an analyte indicator, a drug-eluting matrix, and one or more therapeutic agents. The analyte indicator may cover at least a portion of the sensor housing. The analyte indicator may include one or more indicator molecules that reversibly bind the analyte and exhibit a detectable property indicative of whether the analyte is bound. The drug-eluting matrix may cover at least a portion of the analyte indicator. The drug-eluting polymer matrix may include one or more openings configured to allow the medium to pass through the drug-eluting matrix and come into contact with the analyte indicator. The one or more therapeutic agents may reduce deterioration of the analyte indicator and may be dispersed within the drug-eluting matrix.

In some embodiments, the sensor may be implantable within a living animal. In some embodiments, the drug-eluting matrix may cover at least a portion of the sensor housing. In some embodiments, one or more of the therapeutic agents may be incorporated within the drug-eluting matrix via one or more covalent bonds that break in the presence of aqueous media and release the one or more therapeutic agents.

In some embodiments, one or more of the therapeutic agents may ne incorporated within the drug-eluting matrix via one or more covalent bonds that break through exposure to light and release the one or more therapeutic agents. In some embodiments, the sensor may include a light source, and the covalent bonds may break through exposure to light emitted by the light source.

In some embodiments, the one or more therapeutic agents may include an anti-inflammatory drug. In some embodiments, the anti-inflammatory drug may be a non-steroidal anti-inflammatory drug. In some embodiments, the non-steroidal anti-inflammatory drug may be acetylsalicylic acid.

In some embodiments, the non-steroidal anti-inflammatory drug may be isobutylphenylpropanoic acid.

In some embodiments, the one or more therapeutic agents may include a glucocorticoid. In some embodiments, one or more therapeutic agents may include one or more of dexamethasone, triamcinolone, betamethasone, methylprednisolone, beclometasone, fludrocortisone, derivatives thereof, and analogs thereof. In some embodiments, the one or more therapeutic agents may reduce oxidation of the analyte indicator. In some embodiments, the analyte indicator may be a graft including indicator molecules.

In some embodiments, the sensor may include a layer of a catalyst capable of converting hydrogen peroxide into water and oxygen on at least a portion of the analyte indicator. In some embodiments, the sensor may further include a light source and a photodetector. The light source may be within the sensor housing and may be configured to emit excitation light, the photodetector may be within the sensor housing, and the photodetector may be sensitive to light emitted by the one or more indicator molecules and configured to generate a signal indicative of the amount of the analyte in the medium within the living animal.

In some embodiments, the one or more openings may include a plurality of openings. In some embodiments, the one or more openings may include one or more openings having a circular, oval, square, pear, or diamond shape. In some embodiments, the one or more openings may include relatively large openings and relatively small openings. In some embodiments, the one or more openings may include rows of openings.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
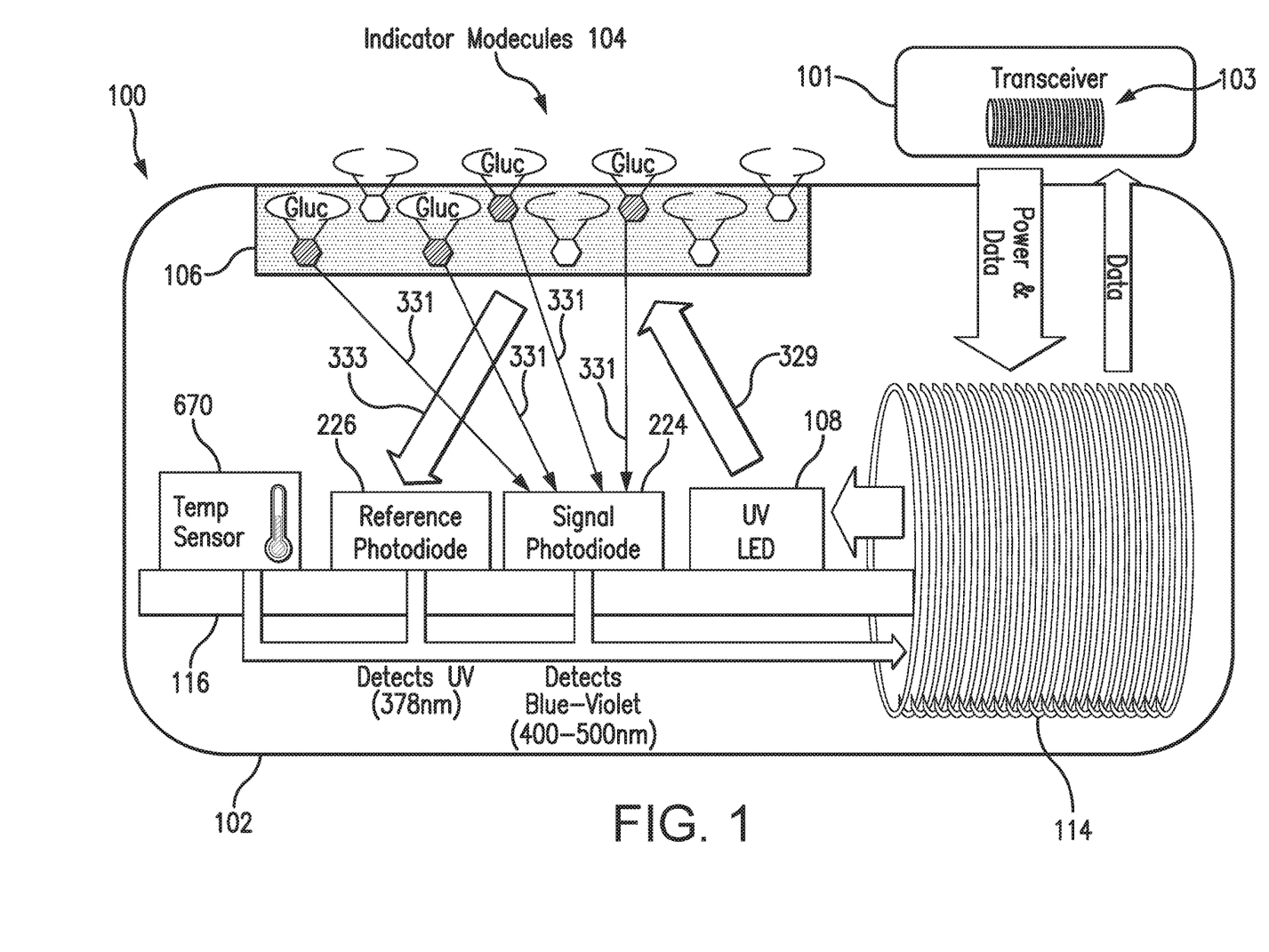
FIG. 1 is a schematic view illustrating a sensor system embodying aspects of the present invention.

FIG. 1 is a schematic view of an exemplary analyte monitoring system embodying aspects of the present invention. The analyte monitoring system may be a continuous analyte monitoring system (e.g., a continuous glucose monitoring system). In some embodiments, the analyte monitoring system may include one or more of an analyte sensor 100 and a transceiver 101.

In some embodiments, the sensor 100 may be small, fully subcutaneously implantable sensor measures analyte (e.g., glucose) concentrations in a medium (e.g., interstitial fluid) of a living animal (e.g., a living human). In some embodiments, the sensor 100 may be implanted, for example, in a living animal's arm, wrist, leg, abdomen, peritoneum, or other region of the living animal suitable for sensor implantation. For example, in one non-limiting embodiment, the sensor 100 may be implanted beneath the skin (i.e., in the subcutaneous or peritoneal tissues). However, it is not required that the sensor 100 be fully a fully implantable sensor, and, in some alternative embodiments, the sensor 100 may be a partially implantable (e.g., transcutaneous) sensor or a fully external sensor.

In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte concentrations) wirelessly (e.g., via a Bluetooth™ communication standard such as, for example and without limitation Bluetooth Low Energy) to a hand held application running on a display device (e.g., smartphone). In some embodiments, the analyte monitoring system may include a web interface for plotting and sharing of uploaded data.

In some embodiments, as illustrated in FIG. 1, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive sensor data (e.g., measurement information) from the sensor 100. For example, in a non-limiting embodiment, the transceiver 101 may receive sensor data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 1, the sensor 100 may be encased in a sensor housing 102 (i.e., body, shell, capsule, or encasement), which may be rigid and biocompatible. The sensor 100 may include an analyte indicator 106, such as, for example, a polymer graft coated, diffused, adhered, or embedded on or in at least a portion of the exterior surface of the sensor housing 102. The analyte indicator 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator 106. In some embodiments, the indicator molecules 104 may reversibly bind the analyte and exhibit a detectable property indicative of whether the analyte is bound. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting matrix 428 that disperses one or more therapeutic agents (e.g., an anti-inflammatory drug).

In some embodiments, as illustrated in FIG. 1, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Figure 2:
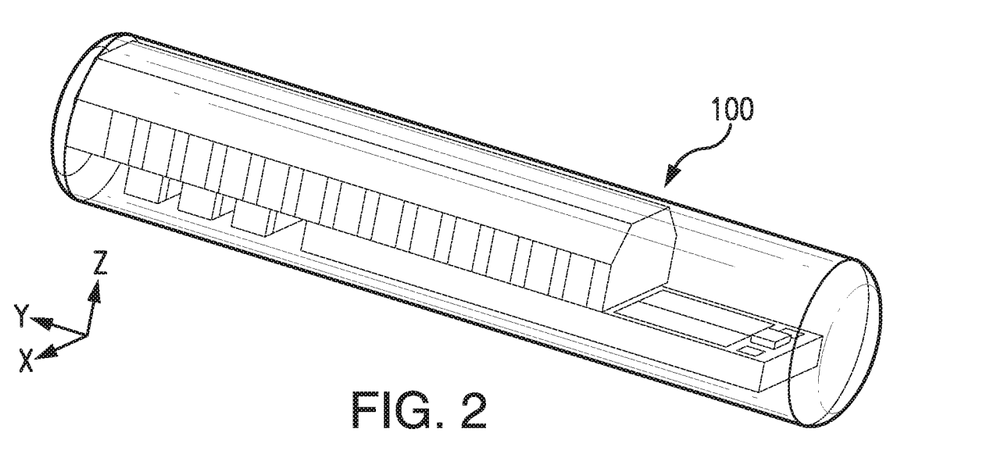
FIG. 2 illustrates a perspective view of a sensor embodying aspects of the present invention.

Although in some embodiments, as illustrated in FIG. 1, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 3:
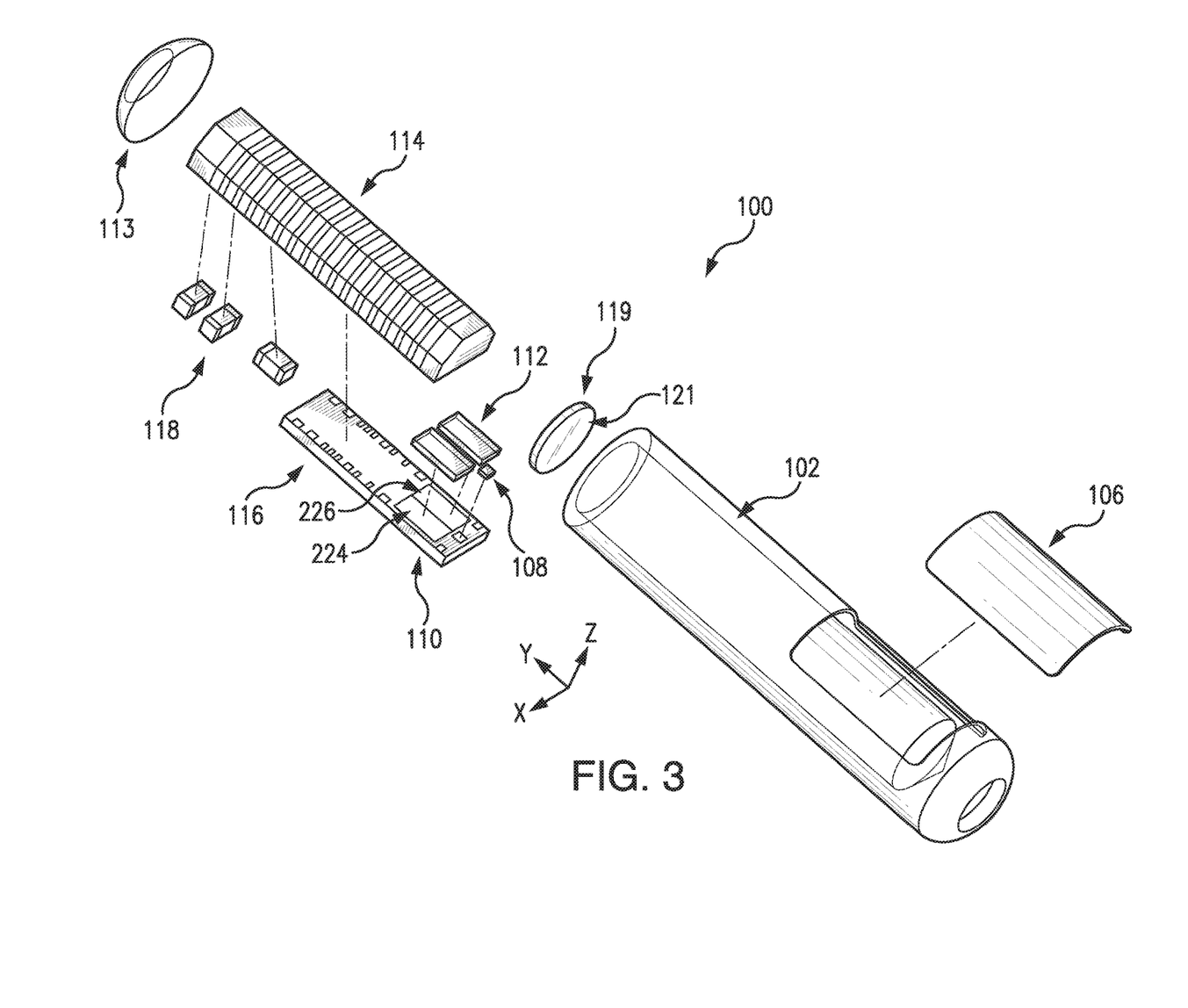
FIG. 3 illustrates an exploded view of a sensor embodying aspects of the present invention.

FIGS. 2 and 3 illustrate a non-limiting embodiment of a sensor 100 embodying aspects of the present invention that may be used in the sensor system illustrated in FIG. 1. FIGS. 2 and 3 illustrate perspective and exploded views, respectively, of the non-limiting embodiment of the sensor 100.

In some embodiments, as illustrated in FIG. 3, the sensor housing 102 may include an end cap 113. In some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, as illustrated in FIG. 3, the sensor 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from exiting the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

The specific composition of the analyte indicator 106 and the indicator molecules 104 may vary depending on the particular analyte the sensor is to be used to detect and/or where the sensor is to be used to detect the analyte (e.g., in the in subcutaneous tissues, blood, or peritoneum). Preferably, however, the analyte indicator 106 should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

The implantation or insertion of a medical device, such as a bio-sensor, into a user/patient's body can cause the body to exhibit adverse physiological reactions that are detrimental to the functioning of the device. The reactions may range from infections due to implantation surgery to the immunological response of a foreign object implanted in the body. That is, the performance of the implantable bio-sensor can be hindered or permanently damaged in vivo via the immunological response to an infection or the device itself. In particular, the performance of the analyte indicator may be deteriorated by the immunological response of the body into which the sensor 100 is implanted. For example, as explained above, white blood cells, including neutrophils, may attack an implanted sensor 100. The neutrophils release, inter alia, hydrogen peroxide, which may degrade indicator molecules 104 (e.g., by oxidizing a boronate group of an indicator molecule and disabling the ability of the indicator molecule to bind glucose).

Figure 4A:
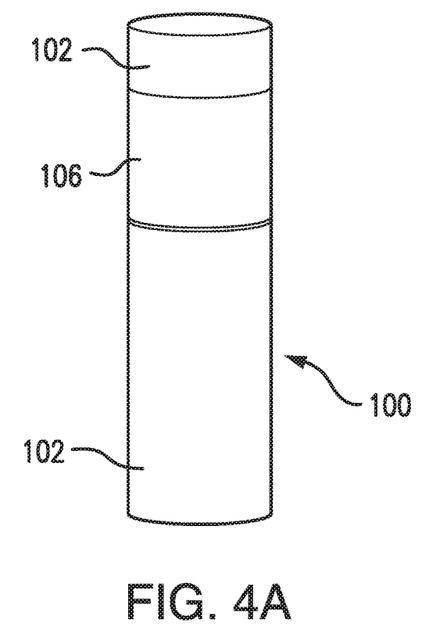
FIGS. 4A and 4B illustrate how a drug-eluting matrix may be applied directly on an analyte indicator of an analyte sensor in accordance with embodiments of the present invention.
Figure 4B:
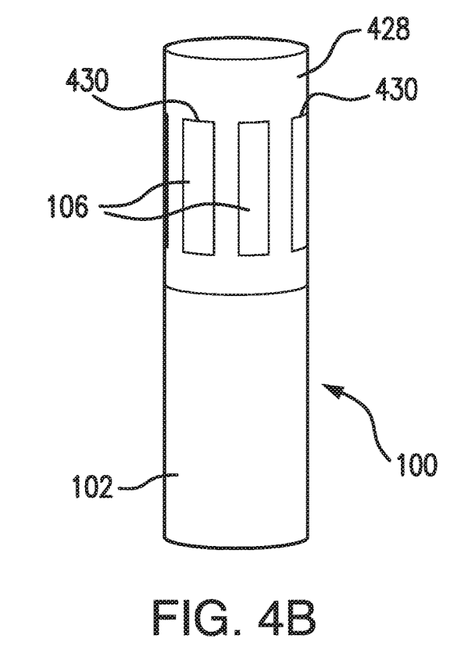
Figure 5A:
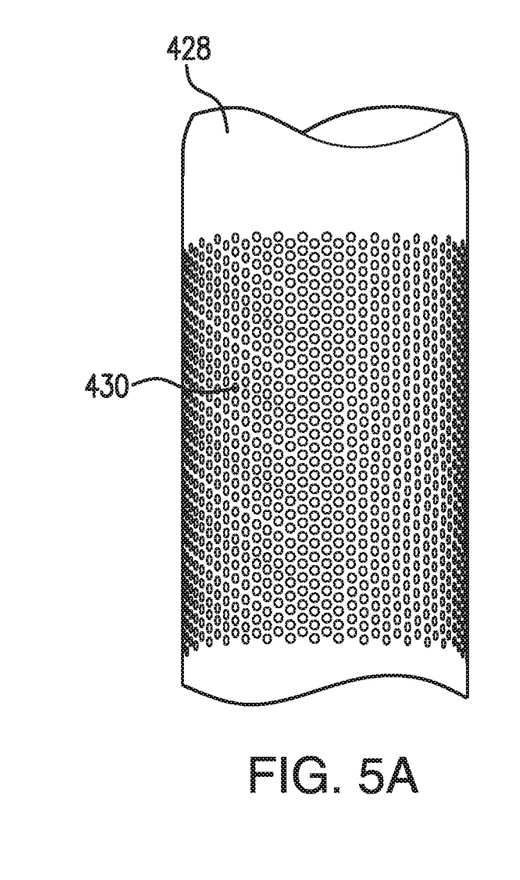
FIGS. 5A-5C illustrate drug-eluting matrices embodying aspects of the present invention.
Figure 5B:
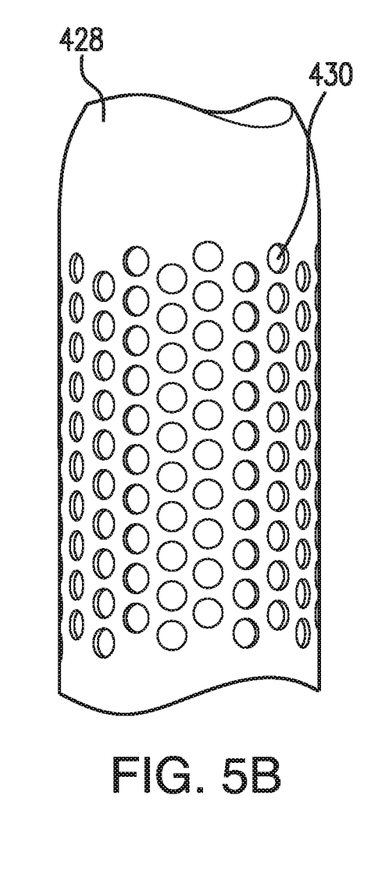
Figure 5C:
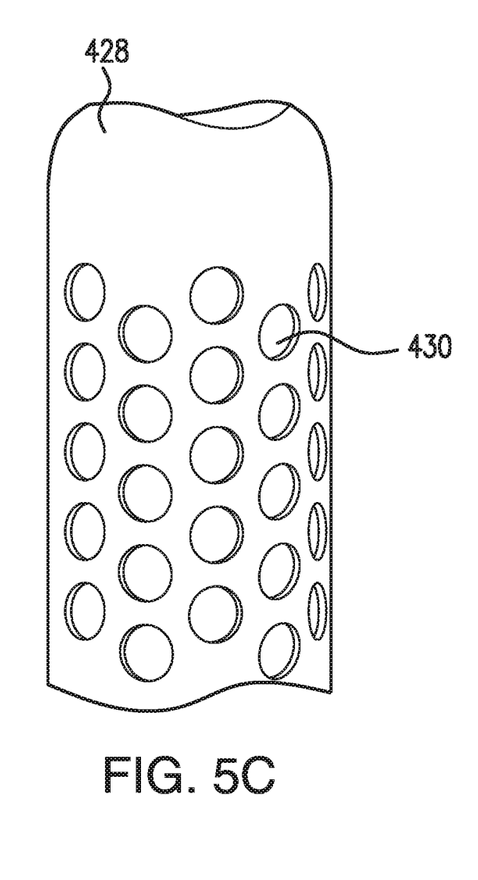

In some embodiments, as shown in FIGS. 4A and 4B, one or more drug-eluting matrices 428 may be applied on an analyte indicator 106 of an analyte sensor 100. FIG. 4A illustrates a non-limiting embodiment of a sensor 100 to which a drug-eluting matrix 428 is to be applied, and FIG. 4B illustrates the non-limiting embodiment of the sensor 100 after the drug-eluting matrix 428 has been applied. In some embodiments, as illustrated in FIG. 4B, the drug-eluting matrix 428 may be applied directly on the analyte indicator 106 of the sensor 100. In some embodiments, as illustrated in FIG. 4B, after application to the sensor 100, the drug-eluting matrix 428 may cover at least a portion of the analyte indicator 106. In some non-limiting embodiments, the drug-eluting matrix 428 may additionally cover at least a portion of the sensor housing 102. In some non-limiting embodiments, the drug-eluting matrix 428 may be a drug-eluting polymer matrix (e.g., an inert polymer matrix).

In some embodiments, as shown in FIG. 4B, the drug-eluting matrix 428 may include one or more openings 430. In some embodiments, the one or more openings 430 may be configured to provide a medium (e.g., ISF, blood, or intra-peritoneal fluid) containing the analyte (e.g., glucose) with access to the analyte indicator 106. In some embodiments, the one or more openings 430 may be configured to allow the analyte-containing medium to pass through the drug-eluting matrix 428 and come in contact with the analyte indicator 106.

FIGS. 4B-9 illustrate various non-limiting embodiments of a drug-eluting matrix 428 embodying aspects of the present invention. In some embodiments, as shown in FIGS. 4B-5C, the drug-eluting matrix 428 may be closed on one end such that the drug-eluting matrix 428 is configured to cover one end of the sensor 100. In some non-limiting embodiments, the closed end of the drug-eluting matrix 428 may rest against one end of the sensor housing 102. In some non-limiting embodiments, the closed end of the drug-eluting matrix 428 may rest against the end of the sensor housing 102 that does not have the end cap 113. However, it is not required that the drug-eluting matrix 428, and, in some alternative embodiments, as shown in FIGS. 6-9, the drug-eluting matrix 428 may be open on both ends. In these alternative embodiments, as shown in FIGS. 6-9, the drug-eluting matrix 428 may have a cylindrical sleeve shape.

In some embodiments, as illustrated in FIG. 4B, the one or more openings 430 may have a rectangular shape. However, this is not required, and, in some alternative embodiments, the openings 430 may have a different shape. For example and without limitation, in some alternative embodiments, the one or more openings 430 may have a circular (see FIGS. 5A-5C and 8), oval (see FIGS. 6 and 9), square, pear, or diamond shape. Moreover, in some embodiments, the openings 403 may have more than one shape (e.g., a drug-eluting matrix 428 may have circular and oval openings as in FIG. 7).

Figure 6:
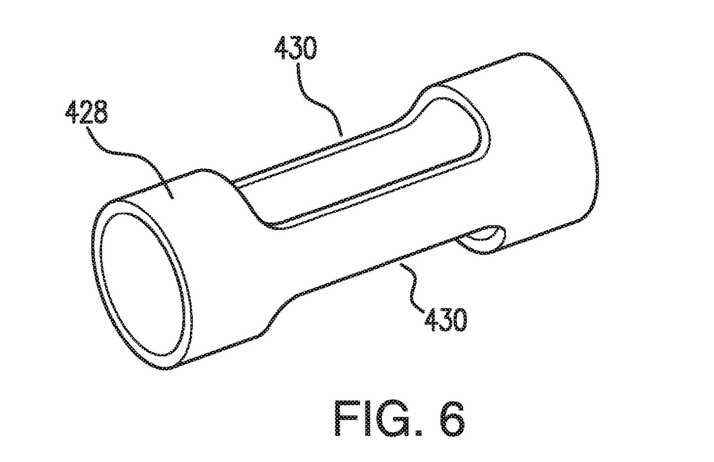
FIG. 6 illustrates a drug eluting matrix embodying aspects of the present invention.
Figure 7:
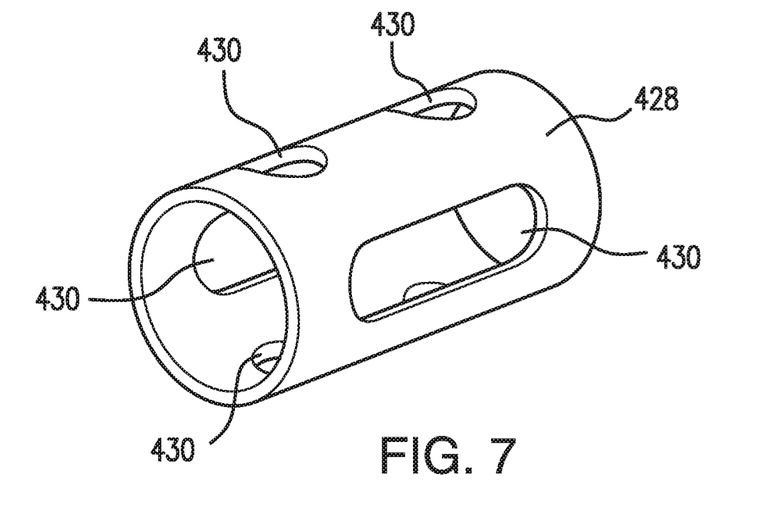
FIG. 7 illustrates a drug eluting matrix embodying aspects of the present invention.
Figure 8:
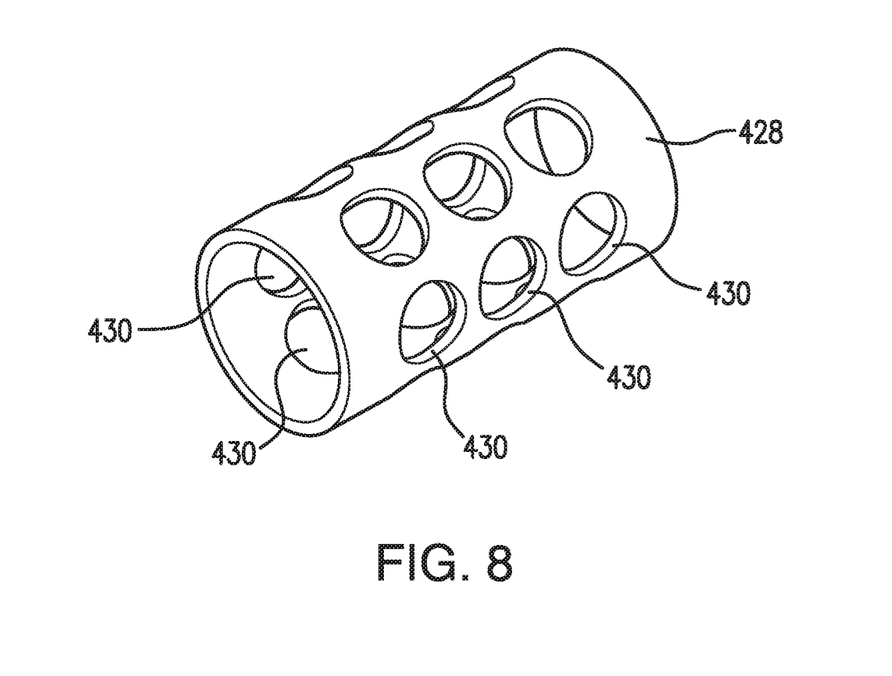
FIG. 8 illustrates a drug eluting matrix embodying aspects of the present invention.
Figure 9:
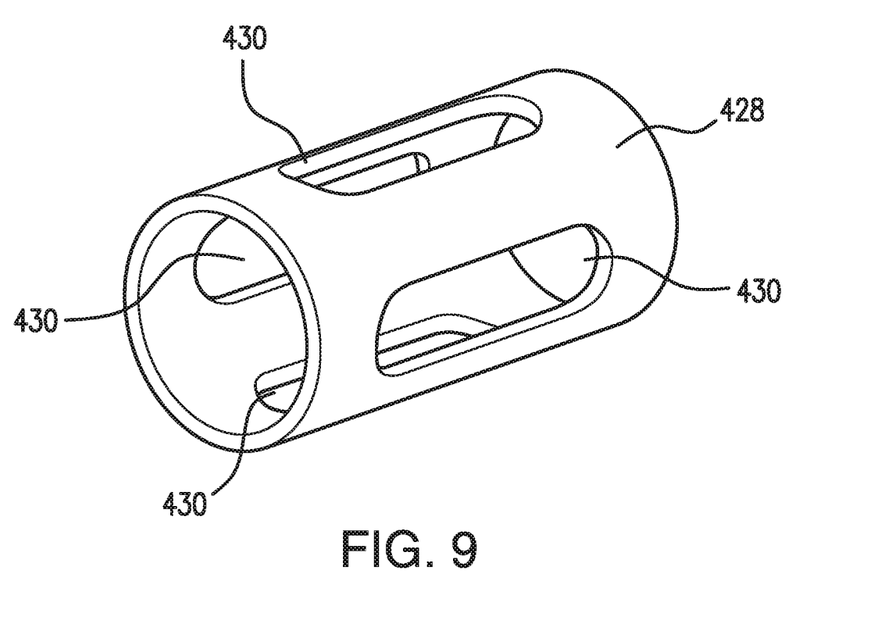
FIG. 9 illustrates a drug eluting matrix embodying aspects of the present invention.

In various embodiments of the drug-eluting matrix 428, as shown in FIGS. 4B-9, the number, shape, and/or size of the openings 430 may vary. In some embodiments, as shown in FIG. 5A, the drug-eluting matrix 428 may have many small openings 430 (e.g., openings having a diameter of 100 μm). In other embodiments, as shown in FIG. 5B, the drug-eluting matrix 428 may have fewer openings 430, and the openings 430 may be bigger (e.g., openings having a diameter of 400 μm). In still other embodiments, as shown in FIG. 5C, the drug-eluting matrix 428 may have even fewer openings 430, and the openings 430 may be even bigger (e.g., openings having a diameter of 700 μm). In some embodiments, as shown in FIG. 6, the drug-eluting matrix 428 may have two very large openings 430. In some embodiments, as shown in FIG. 7, the drug-eluting matrix 428 may have a number of relatively large openings 430 (e.g., two oval openings) and a number of relatively small openings 430 (e.g., four circular openings). In some embodiments, the drug-eluting matrix 428 may have a number of rows of openings 430 (e.g., six rows of three circular openings 430). In some embodiments, as shown in FIG. 9, the drug-eluting matrix 428 may have four large openings 430.

In some embodiments, the sensor 100 may include a drug-eluting matrix 428 that covers at least a portion of the analyte indicator 106. In some embodiments, the drug-eluting matrix 428 may also cover at least a portion of the sensor housing 102. In some embodiments, one or more therapeutic agents may be dispersed from the drug-eluting matrix 428. In some embodiments, the one or more therapeutic agents may reduce or stop the migration of neutrophils from entering the wound space and, thus, reduce or stop the production of hydrogen peroxide and/or fibrotic encapsulation. Accordingly, in some embodiments, the one or more therapeutic agents may reduce deterioration of the analyte indicator 106 (e.g., polymer graft).

In some embodiments, the surface area of the drug-eluting matrix 428 may be such that a sufficient amount of the one or more therapeutic agents is released. In some embodiments, the combined area of the one or more openings 430 may be such that a sufficient surface area of the analyte indicator 106 is exposed to the analyte-containing medium (e.g., interstitial fluid).

In some non-limiting embodiments, the analyte indicator 106 (e.g., polymer graft) may a have thin layer (e.g., 10 nm) on the outside of the graft 106. The thin layer may protect against indicator molecule degradation. The thin layer may be platinum, and the platinum may be sputtered onto the outside surface of the analyte indicator 106, which may include the indicator molecules 104. Platinum rapidly catalyzes the conversion of hydrogen peroxide into water and oxygen, which are harmless to the sensor. The rate of this reaction is much faster than the boronate oxidation; thus, the platinum would provide protection against oxidation by reactive oxygen species. Although platinum is the catalyst of the conversion of hydrogen peroxide into water and oxygen in some embodiments, in alternative embodiments, other catalysts of this reaction, such as, for example, palladium or catalase, may be used for the thin layer instead of or in addition to platinum.

In some embodiments, the one or more therapeutic agents, which may be dispersed from the drug-eluting matrix 428, may include one or more anti-inflammatory drugs, such as, for example, non-steroidal anti-inflammatory drug (e.g., acetylsalicylic acid (aspirin) and/or isobutylphenylpropanoic acid (ibuprofen)). In some non-limiting embodiments, the one or more therapeutic agents dispersed from the drug-eluting matrix 428 may include one or more glucocorticoids. In some non-limiting embodiments, the one or more therapeutic agents may include one or more of dexamethasone, triamcinolone, betamethasone, methylprednisolone, beclometasone, fludrocortisone, derivatives thereof, and analogs thereof. In some embodiments, the one or more therapeutic agents may reduce the production of hydrogen peroxide by neutrophils and macrophages. In some embodiments, the one or more therapeutic agents may reduce deterioration of the analyte indicator 106.

Figure 10:
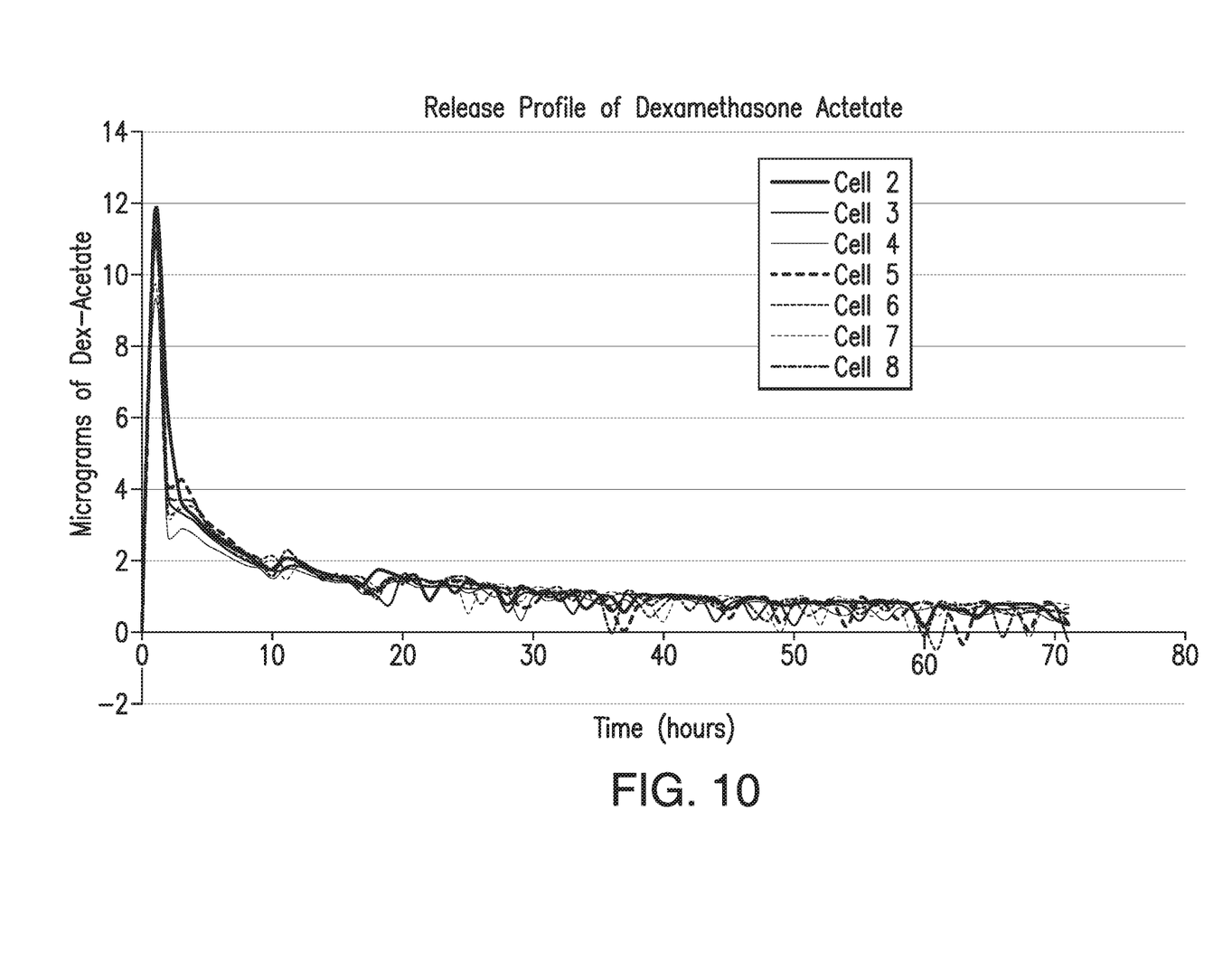
FIG. 10 illustrates the release profile of dexamethasone acetate from a drug-eluting matrix according to one embodiment.

In some non-limiting embodiments, the drug-eluting matrix 428 may release the one or more therapeutic agents distributed throughout the matrix 428 in a controlled manner. For instance, in various embodiments, the drug-eluting matrix 428 may release the one or more therapeutic agents in a controlled manner over a period of hours, days, weeks, or months. FIG. 10 illustrates the release profile of dexamethasone acetate from a drug-eluting matrix 428 according to one non-limiting embodiment.

In some embodiments, the one or more therapeutic agents may be chemically incorporated within the drug-eluting matrix 428. In some non-limiting embodiments, one or more therapeutic agents may be incorporated within the drug-eluting matrix 428 via covalent bonds. The drug-eluting matrix 428 may release the one or more therapeutic agents when one or more of the covalent bonds are broken. For example, in one non-limiting embodiment, the covalent bonds may break in the presence of water (e.g., in the presence of water in the interstitial fluid, blood, or intraperitoneal fluid). However, this is not required, and, in some alternative embodiments, the covalent bonds may additionally or alternatively break through exposure to ultraviolet or visible light. In some non-limiting embodiments, the covalent bonds may break through exposure to light emitted by the light source 108. For example, in one embodiment, exposure to the excitation light 329 (e.g., having a wavelength of approximately 378 nm) emitted by the light source 108 may cause the covalent bonds to break. Moreover, the light source 108 may be controlled to emit light in a manner (e.g., blinking at specific intervals and/or intensities) that alters (e.g., increases the rate at which one or more therapeutic agents are released) the elution profile of the one or more therapeutic agents (e.g., to maximize effectiveness in preventing oxidation of the indicator species). In some embodiments, a wavelength in a specific range (e.g., 150 nm-1000 nm or 300-600 nm) may be necessary to photocleave (i.e., break the covalent bonds and release), and the wavelength of the light emitted by the light source 108 of the sensor 100 may be within in the specific range.

An implanted sensor 100 including a drug-eluting matrix 428 may have improved performance over a sensor that does not include a drug-eluting matrix. For instance, the controlled release of one or more therapeutic agents (e.g., by a drug-eluting matrix 428) may have improved longevity and functionality.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A sensor for measurement of an analyte in a medium within a living animal, the sensor comprising:
   a sensor housing;
   an analyte indicator covering at least a portion of the sensor housing, wherein the analyte indicator comprises one or more indicator molecules that reversibly bind the analyte and exhibit a detectable property indicative of whether the analyte is bound;
   a drug-eluting matrix that covers only a portion of the analyte indicator, wherein the drug-eluting matrix includes one or more openings configured to allow the medium to pass through the drug-eluting matrix and come into contact with the analyte indicator, and the one or more openings of the drug-eluting matrix result in the drug-eluting matrix not covering one or more portions of the analyte indicator; and
   one or more therapeutic agents that reduce deterioration of the analyte indicator and are dispersed within the drug-eluting matrix.

2. The sensor of claim 1, wherein the sensor is implantable within a living animal.

3. The sensor of claim 1, wherein the drug-eluting matrix covers at least a portion of the sensor housing.

4. The sensor of claim 1, wherein the druq-elutinq matrix is a druq-elutinq polymer matrix, and wherein one or more of the therapeutic agents are incorporated within the drug-eluting polymer matrix via one or more covalent bonds that break in the presence of aqueous media and release the one or more therapeutic agents.

5. The sensor of claim 1, wherein the druq-elutinq matrix is a druq-elutinq polymer matrix, and wherein one or more of the therapeutic agents are incorporated within the drug-eluting polymer matrix via one or more covalent bonds that break through exposure to light and release the one or more therapeutic agents.

6. The sensor of claim 5, further comprising a light source, wherein the covalent bonds break through exposure to light emitted by the light source.

7. The sensor of claim 1, wherein the one or more therapeutic agents include an anti-inflammatory drug.

8. The sensor of claim 7, wherein the anti-inflammatory drug is a non-steroidal anti-inflammatory drug.

9. The sensor of claim 8, wherein the non-steroidal anti-inflammatory drug is acetylsalicylic acid.

10. The sensor of claim 8, wherein the non-steroidal anti-inflammatory drug is isobutylphenylpropanoic acid.

11. The sensor of claim 1, wherein the one or more therapeutic agents include a glucocorticoid.

12. The sensor of claim 1, wherein the one or more therapeutic agents include one or more of dexamethasone, triamcinolone, betamethasone, methylprednisolone, beclometasone, fludrocortisone, derivatives thereof, and analogs thereof.

13. The sensor of claim 1, wherein the one or more therapeutic agents reduce oxidation of the analyte indicator.

14. The sensor of claim 1, wherein the analyte indicator is a graft including indicator molecules.

15. The sensor of claim 1, further comprising a layer of a catalyst capable of converting hydrogen peroxide into water and oxygen on at least a portion of the analyte indicator.

16. The sensor of claim 1, further comprising:
a light source within the sensor housing configured to emit excitation light; and
a photodetector within the sensor housing, wherein the photodetector is sensitive to light emitted by the one or more indicator molecules and configured to generate a signal indicative of the amount of the analyte in the medium within the living animal.

17. The sensor of claim 1, wherein the one or more openings comprise a plurality of openings.

18. The sensor of claim 1, wherein the one or more openings comprise one or more openings having a circular, oval, square, pear, or diamond shape.

19. The sensor of claim 1, wherein the one or more openings comprise relatively large openings and relatively small openings.

20. The sensor of claim 1, wherein the one or more openings comprise rows of openings.

* * * * *